US008057399B2

(12) United States Patent
Greenland et al.

(10) Patent No.: US 8,057,399 B2
(45) Date of Patent: Nov. 15, 2011

(54) ANCHOR FOR AN IMPLANTABLE SENSOR

(75) Inventors: John S. Greenland, San Diego, CA (US); Peter J. D'Aquanni, Murrieta, CA (US); William S. Chin, Moreno Valley, CA (US); Charles R. Peterson, Murrieta, CA (US); Kevin M. Magrini, Temecula, CA (US); Jessie Delgado, Murrieta, CA (US); Benjamin R. Fruland, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1096 days.

(21) Appl. No.: 11/855,725

(22) Filed: Sep. 14, 2007

(65) Prior Publication Data

US 2008/0071178 A1   Mar. 20, 2008

Related U.S. Application Data

(60) Provisional application No. 60/844,821, filed on Sep. 15, 2006.

(51) Int. Cl.
*A61B 5/02*   (2006.01)
*A61F 2/06*   (2006.01)

(52) U.S. Cl. ..... 600/488; 623/1.12; 623/1.15; 623/1.16; 623/1.18; 623/1.2

(58) Field of Classification Search ............. 600/486, 600/488, 504, 505; 623/1.2
See application file for complete search history.

(56) References Cited

U.S. PATENT DOCUMENTS

| 3,874,388 A | 4/1975 | King et al. |
| 4,391,124 A | 7/1983 | Drost et al. |
| 4,407,296 A * | 10/1983 | Anderson ............ 600/488 |
| 4,485,813 A | 12/1984 | Anderson et al. |
| 4,492,107 A | 1/1985 | Sandhu |
| 4,672,976 A | 6/1987 | Kroll |

(Continued)

FOREIGN PATENT DOCUMENTS

EP   0897690   2/1999

(Continued)

OTHER PUBLICATIONS

Goodall, Eleanor V. et al., "Position-Seletive Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

(Continued)

*Primary Examiner* — Miranda Le
*Assistant Examiner* — Scott Gonzalez
(74) *Attorney, Agent, or Firm* — Faegre & Benson LLP (57) ABSTRACT

An anchor for an implantable medical device, for example, and implantable physiologic sensor, includes a proximal hub portion, an intermediate portion extending radially and distally from the hub portion, and a distal portion extending distally from the proximal portion and adapted to engage an inner surface of a target vessel for securing the implantable medical device therein. The anchor can assume a collapsed configuration for delivery through a catheter, and an expanded configuration for fixation within the vessel once deployed. The intermediate portion extends from the proximal portion at an oblique angle, allowing the anchor to be retracted and re-collapsed within the delivery catheter after initial deployment, if re-positioning or removal of the implantable medical device is necessary or desired.

13 Claims, 10 Drawing Sheets

U.S. PATENT DOCUMENTS

| | | | |
|---|---|---|---|
| 4,836,204 A | 6/1989 | Landymore et al. | |
| 4,846,191 A | 7/1989 | Brockway et al. | |
| 4,900,303 A | 2/1990 | Lemelson | |
| 4,917,089 A | 4/1990 | Sideris | |
| 4,966,148 A | 10/1990 | Millar | |
| 5,040,538 A | 8/1991 | Mortazavi | |
| 5,218,965 A | 6/1993 | Ring | |
| 5,284,138 A | 2/1994 | Kujawski | |
| 5,303,207 A | 4/1994 | Brady et al. | |
| 5,334,217 A | 8/1994 | Das | |
| 5,411,551 A | 5/1995 | Winston et al. | |
| 5,415,630 A | 5/1995 | Gory et al. | |
| 5,451,235 A | 9/1995 | Lock et al. | |
| 5,604,531 A | 2/1997 | Iddan et al. | |
| 5,634,936 A | 6/1997 | Linden et al. | |
| 5,656,036 A | 8/1997 | Palmaz | |
| 5,662,711 A | 9/1997 | Douglas | |
| 5,704,352 A | 1/1998 | Tremblay et al. | |
| 5,725,552 A | 3/1998 | Kotula et al. | |
| 5,733,313 A | 3/1998 | Barreras, Sr. et al. | |
| 5,772,669 A | 6/1998 | Vrba | |
| 5,775,331 A | 7/1998 | Raymond et al. | |
| 5,824,053 A | 10/1998 | Khosravi et al. | |
| 5,833,603 A | 11/1998 | Kovacs et al. | |
| 5,855,563 A | 1/1999 | Kaplan et al. | |
| 5,860,923 A | 1/1999 | Lenker et al. | |
| 5,891,154 A | 4/1999 | Loeffler | |
| 5,967,980 A | 10/1999 | Ferre et al. | |
| 5,967,986 A | 10/1999 | Cimochowski et al. | |
| 5,967,989 A | 10/1999 | Cimochowski et al. | |
| 6,002,969 A | 12/1999 | Machek et al. | |
| 6,015,386 A | 1/2000 | Kensey et al. | |
| 6,015,387 A | 1/2000 | Schwartz et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Feierbach | |
| 6,097,984 A | 8/2000 | Douglas | |
| 6,106,464 A | 8/2000 | Bass et al. | |
| 6,140,740 A | 10/2000 | Porat et al. | |
| 6,159,156 A | 12/2000 | Van Bockel | |
| 6,179,858 B1 | 1/2001 | Squire et al. | |
| 6,193,745 B1 | 2/2001 | Fogarty et al. | |
| 6,214,025 B1 * | 4/2001 | Thistle et al. | 606/200 |
| 6,231,516 B1 | 5/2001 | Keilman | |
| 6,236,889 B1 | 5/2001 | Soykan et al. | |
| 6,239,724 B1 | 5/2001 | Doron et al. | |
| 6,240,312 B1 | 5/2001 | Alfano et al. | |
| 6,246,898 B1 | 6/2001 | Vesely et al. | |
| 6,277,078 B1 | 8/2001 | Porat et al. | |
| 6,278,790 B1 | 8/2001 | Davis et al. | |
| 6,309,350 B1 | 10/2001 | VanTassel | |
| 6,328,699 B1 | 12/2001 | Eigler et al. | |
| 6,331,163 B1 | 12/2001 | Kaplan | |
| 6,379,308 B1 | 4/2002 | Brockway et al. | |
| 6,409,674 B1 | 6/2002 | Brockway et al. | |
| 6,416,474 B1 | 7/2002 | Penner et al. | |
| 6,432,050 B1 | 8/2002 | Porat et al. | |
| 6,442,413 B1 | 8/2002 | Silver | |
| 6,447,522 B2 | 9/2002 | Gambale et al. | |
| 6,475,170 B1 | 11/2002 | Doron et al. | |
| 6,486,588 B2 | 11/2002 | Doron et al. | |
| 6,527,780 B1 | 3/2003 | Wallace et al. | |
| 6,543,272 B1 | 4/2003 | Vitek | |
| 6,585,763 B1 | 7/2003 | Keilman et al. | |
| 6,592,553 B2 | 7/2003 | Zhang et al. | |
| 6,628,989 B1 | 9/2003 | Penner et al. | |
| 6,645,143 B2 | 11/2003 | VanTassel et al. | |
| 6,660,021 B1 * | 12/2003 | Palmer et al. | 606/200 |
| 6,685,638 B1 | 2/2004 | Taylor et al. | |
| 6,699,186 B1 | 3/2004 | Wolinsky et al. | |
| 6,702,847 B2 | 3/2004 | DiCarlo | |
| 6,730,108 B2 | 5/2004 | Van Tassel et al. | |
| 6,738,671 B2 | 5/2004 | Christophersom et al. | |
| 6,743,173 B2 | 6/2004 | Penner et al. | |
| 6,746,404 B2 | 6/2004 | Schwartz | |
| 6,747,916 B1 | 6/2004 | Fleury et al. | |
| 6,755,855 B2 | 6/2004 | Yurek et al. | |
| 6,764,446 B2 | 7/2004 | Wolinsky et al. | |
| 6,783,499 B2 | 8/2004 | Schwartz | |
| 6,800,060 B2 | 10/2004 | Marshall | |
| 6,840,956 B1 | 1/2005 | Wolinsky et al. | |
| 6,855,115 B2 | 2/2005 | Fonseca et al. | |
| 6,868,288 B2 | 3/2005 | Thompson | |
| 6,890,303 B2 | 5/2005 | Fitz | |
| 6,899,729 B1 | 5/2005 | Cox et al. | |
| 6,904,308 B2 | 6/2005 | Frisch et al. | |
| 6,920,347 B2 | 7/2005 | Simon et al. | |
| 6,926,670 B2 | 8/2005 | Rich | |
| 6,934,573 B1 | 8/2005 | Glukhovsky et al. | |
| 6,950,690 B1 | 9/2005 | Meron et al. | |
| 6,958,034 B2 | 10/2005 | Iddan | |
| 6,970,742 B2 | 11/2005 | Mann et al. | |
| 6,972,017 B2 | 12/2005 | Smith et al. | |
| 6,984,205 B2 | 1/2006 | Gazdzinski | |
| 7,001,329 B2 | 2/2006 | Kobayashi et al. | |
| 7,009,634 B2 | 3/2006 | Iddan et al. | |
| 7,011,671 B2 | 3/2006 | Welch | |
| 7,024,248 B2 | 4/2006 | Penner et al. | |
| 7,033,322 B2 | 4/2006 | Silver | |
| 7,035,684 B2 | 4/2006 | Lee | |
| 7,039,453 B2 | 5/2006 | Mullick et al. | |
| 7,060,038 B2 | 6/2006 | Letort et al. | |
| 7,064,472 B2 | 6/2006 | Pelrine et al. | |
| 7,065,409 B2 | 6/2006 | Mazar | |
| 7,083,822 B2 | 8/2006 | Brightbill | |
| 7,116,352 B2 | 10/2006 | Yaron | |
| 7,118,529 B2 | 10/2006 | Glukhovsky et al. | |
| 7,118,531 B2 | 10/2006 | Krill | |
| 7,131,986 B2 | 11/2006 | Sirhan et al. | |
| 7,160,258 B2 | 1/2007 | Imran et al. | |
| 7,181,261 B2 | 2/2007 | Silver et al. | |
| 7,198,603 B2 | 4/2007 | Penner et al. | |
| 7,211,045 B2 | 5/2007 | Dala-Krishna et al. | |
| 7,273,457 B2 | 9/2007 | Penner | |
| 7,283,874 B2 | 10/2007 | Penner | |
| 7,308,319 B2 | 12/2007 | Lovett et al. | |
| 7,338,512 B2 * | 3/2008 | McGuckin et al. | 606/200 |
| 7,347,868 B2 | 3/2008 | Burnett et al. | |
| 7,437,193 B2 | 10/2008 | Parramon et al. | |
| 7,452,334 B2 | 11/2008 | Gianchandani et al. | |
| 7,477,946 B2 | 1/2009 | Tockman et al. | |
| 7,780,694 B2 * | 8/2010 | Palmer et al. | 606/200 |
| 7,850,708 B2 * | 12/2010 | Pal | 606/200 |
| 2002/0123672 A1 | 9/2002 | Christophersom et al. | |
| 2002/0165601 A1 | 11/2002 | Clerc | |
| 2002/0183628 A1 | 12/2002 | Reich et al. | |
| 2002/0188207 A1 | 12/2002 | Richter | |
| 2003/0114735 A1 | 6/2003 | Silver et al. | |
| 2003/0114897 A1 | 6/2003 | Von Arx et al. | |
| 2003/0139796 A1 | 7/2003 | Sequin et al. | |
| 2003/0200031 A1 | 10/2003 | Kok | |
| 2004/0006377 A1 | 1/2004 | Behm | |
| 2004/0116992 A1 | 6/2004 | Wardle et al. | |
| 2004/0147969 A1 | 7/2004 | Mann et al. | |
| 2004/0176672 A1 | 9/2004 | Silver et al. | |
| 2004/0204744 A1 | 10/2004 | Penner et al. | |
| 2004/0215228 A1 | 10/2004 | Simpson et al. | |
| 2005/0080472 A1 | 4/2005 | Atkinson et al. | |
| 2005/0115561 A1 | 6/2005 | Stahmann et al. | |
| 2005/0124875 A1 | 6/2005 | Kawano et al. | |
| 2005/0136385 A1 | 6/2005 | Mann et al. | |
| 2005/0149108 A1 | 7/2005 | Cox | |
| 2005/0149128 A1 | 7/2005 | Heil, Jr. et al. | |
| 2005/0149155 A1 | 7/2005 | Scheiner et al. | |
| 2005/0149156 A1 | 7/2005 | Libbus et al. | |
| 2005/0154321 A1 * | 7/2005 | Wolinsky et al. | 600/486 |
| 2005/0165456 A1 | 7/2005 | Mann et al. | |
| 2005/0209678 A1 * | 9/2005 | Henkes et al. | 623/1.12 |
| 2005/0245840 A1 | 11/2005 | Christopherson et al. | |
| 2006/0009818 A1 | 1/2006 | Von Arx et al. | |
| 2006/0047205 A1 | 3/2006 | Ludomirsky et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0079740 A1 | 4/2006 | Silver et al. | |

| | | | | | | |
|---|---|---|---|---|---|---|
| 2006/0089627 | A1 | 4/2006 | Burnett et al. | WO | WO01/87137 | 11/2001 |
| 2006/0089694 | A1 | 4/2006 | Zhang et al. | WO | WO 2004/024034 | 3/2004 |
| 2006/0122522 | A1 | 6/2006 | Chavan et al. | WO | WO 2005/067817 | 7/2005 |
| 2006/0136004 | A1 | 6/2006 | Cowan et al. | WO | WO2006/062725 | 6/2006 |
| 2006/0142819 | A1 | 6/2006 | Penner et al. | WO | WO2007/057739 | 5/2007 |
| 2006/0149329 | A1 | 7/2006 | Penner | WO | WO2007/082115 | 7/2007 |
| 2006/0149330 | A1 | 7/2006 | Mann et al. | WO | 2008002654 | 1/2008 |
| 2006/0178586 | A1 | 8/2006 | Dobak, III | WO | WO2008/057720 | 5/2008 |
| 2006/0206153 | A1 | 9/2006 | Libbus et al. | WO | WO2008/060197 | 5/2008 |
| 2006/0241735 | A1 | 10/2006 | Tockman et al. | WO | WO2008/144191 | 11/2008 |
| 2006/0259085 | A1 | 11/2006 | Zhang et al. | WO | 2009006610 | 1/2009 |
| 2006/0287700 | A1 | 12/2006 | White et al. | | | |
| 2006/0293741 | A1 | 12/2006 | Johnson et al. | | | |
| 2007/0049833 | A1 | 3/2007 | Tearney et al. | | | |
| 2007/0129637 | A1 | 6/2007 | Wolinsky et al. | | | |
| 2007/0156126 | A1 | 7/2007 | Flaherty | | | |
| 2007/0156205 | A1 | 7/2007 | Larson et al. | | | |
| 2007/0162090 | A1 | 7/2007 | Penner | | | |
| 2007/0179583 | A1 | 8/2007 | Goetzinger et al. | | | |
| 2007/0191904 | A1 | 8/2007 | Libbus et al. | | | |
| 2007/0208390 | A1 | 9/2007 | Von Arx et al. | | | |
| 2007/0250126 | A1 | 10/2007 | Maile et al. | | | |
| 2007/0274565 | A1 | 11/2007 | Penner | | | |
| 2008/0071248 | A1 | 3/2008 | Delgado et al. | | | |
| 2008/0071339 | A1 | 3/2008 | Stalker et al. | | | |
| 2008/0108904 | A1 | 5/2008 | Heil | | | |
| 2008/0176271 | A1 | 7/2008 | Silver et al. | | | |
| 2008/0275350 | A1 | 11/2008 | Liao et al. | | | |
| 2008/0283066 | A1 | 11/2008 | Delgado et al. | | | |
| 2009/0054793 | A1 | 2/2009 | Nunez et al. | | | |
| 2009/0171274 | A1 | 7/2009 | Harlev et al. | | | |
| 2009/0270742 | A1 | 10/2009 | Wolinsky et al. | | | |
| 2010/0016840 | A1 | 1/2010 | Stahmann et al. | | | |
| 2010/0210923 | A1 | 8/2010 | Li et al. | | | |

FOREIGN PATENT DOCUMENTS

| | | |
|---|---|---|
| EP | 0928598 | 8/2000 |
| EP | 1068836 | 1/2001 |
| EP | 1488735 | 12/2004 |
| GB | 2333044 | 7/1999 |
| WO | WO83/03348 | 10/1983 |
| WO | WO99/34731 | 7/1999 |
| WO | WO00/16686 | 3/2000 |
| WO | WO00/59376 | 10/2000 |
| WO | WO01/67989 | 9/2001 |

OTHER PUBLICATIONS

International Search Report and Written Opinion issued in PCT/US2010/020756, mailed Sep. 27, 2010.

Invitation to Pay Fees and Partial Search Report issued in PCT/US2010/020756, mailed May 12, 2010.

Holmes et al. "SirolimusEluting Stents vs. *Vascular Brachytherapy for InStent Restenosis Within BareMetal Stents*" JAMA295 (11): 12641273 Mar. 15, 2006.

Sheth et al. "Subacute Thrombosis and Vascular Injury Resulting From SlottedTube Nitinol and Stainless Steel Stents in a Rabbit Carotid Artery Model" Circulation 94: 17331740.

Stone et al. "*PaclitaxelEluting Stents* vs. *Vascular Brachytherapy for InStent Restenosis Within BareMetal Stents*" JAMA 295( 11): 12531263.

Webster's II new Riverside University Dictionary, Riverside Publishing Company, 1994, pp. 421 and 625.

Wenaweser et al. "Stent thrombosis following baremetal stent implantation: success of emergency percutaneous coronary intervention and predictors of adverse outcome" European Heart Journal 26: 11801187 2005.

International Search Report and Written Opinion of international application No. PCT/US2007/078525, mailed May 27, 2008, 12 pp.

Lanning & Shandas, "Development and Validation of Implantable Sensors for Monitoring Function of Prosthetic Heart Valves: In Vitro Studies", Medical & Biological Engineering & Computing, Jul. 2003, vol. 41, issue 4, pp. 416-424.

International Search Report and Written Opinion from PCT/US2008/062229, mailed Jan. 5, 2009.

\* cited by examiner

ANCHOR FOR AN IMPLANTABLE SENSOR

CROSS REFERENCE TO RELATED APPLICATION

The present invention claims priority under 35 U.S.C. §119 to U.S. Provisional Application No. 60/844,821, filed Sep. 15, 2006, which is incorporated herein by reference in its entirety.

TECHNICAL FIELD

The present invention relates to medical devices and methods for anchoring implantable medical devices in the body. In particular, the present invention relates to anchoring devices and methods for anchoring implantable physiologic sensors and other implantable medical devices within a patient's cardiovascular system.

BACKGROUND

Medical devices that can be implanted within a patient's body for monitoring one or more physiological parameters and/or to provide therapeutic functions are known. For example, sensors or transducers can be placed in the body for monitoring a variety of properties, such as temperature, blood pressure, strain, fluid flow, chemical properties, electrical properties, magnetic properties, and the like. In addition, medical devices can be implanted that perform one or more therapeutic functions, such as drug delivery, cardiac pacing, defibrillation, electrical stimulation, and the like.

One parameter of particular interest is blood pressure. One or more implantable pressure sensing modules can be used in conjunction with cardiac rhythm management (CRM) devices to facilitate optimization of CRM device settings. In such systems, the pressure sensing module is delivered transvenously to a target vessel (e.g., the pulmonary artery), and anchored in the vessel using various fixation techniques. Accurate placement of the sensing module is an important factor in accurately and reliably measuring the desired parameter. Additionally, under some circumstances, it becomes necessary to re-position an implantable sensor module after initial deployment, or alternatively, to remove the sensor from the patient entirely.

Thus, a need exists for an apparatus and methods for placing and anchoring implantable medical devices within a patient's body. In particular, there is a need for an anchoring system that can be accurately re-positioned and re-deployed, or in the alternative, removed from the patient's vasculature, after an initial deployment.

SUMMARY

The present invention, in one embodiment, is an implantable sensor assembly configured for delivery through a delivery catheter, the sensor assembly comprising an implantable sensor and an anchor coupled to the sensor and adapted to assume a collapsed configuration within the delivery catheter and an expanded configuration external to the delivery catheter. The anchor includes a proximal hub portion, an intermediate portion hingedly coupled to and extending distally and radially from the hub portion, the intermediate portion configured to assume a generally oblique angle with respect to the hub portion when the anchor is in the expanded configuration, and a distal portion extending distally from the intermediate portion and adapted to engage an inner surface of a vessel when the anchor is in the expanded configuration. The intermediate portion is configured to allow the anchor to be retracted within the delivery catheter and to assume the collapsed configuration after assuming the expanded configuration.

The present invention, in another embodiment, is an implantable sensor assembly comprising a sensor including a housing hermetically enclosing a sensor element, an anchor. The anchor includes a proximal sensor attachment portion coupled to the housing, and radially expandable means extending from the sensor attachment portion for engaging an inner surface of a vessel.

In yet another embodiment, the present invention is a method of deploying an implantable sensor assembly. In one embodiment, the method comprises positioning a distal end of a delivery catheter at a first location within a body lumen. Next, the method includes deploying an anchor portion of the sensor assembly from the distal end of the delivery catheter such that the anchor portion assumes an expanded configuration. The method further includes, in one embodiment, retracting the anchor portion into the delivery catheter such that the anchor portion assumes a collapsed configuration, repositioning the distal end of the delivery catheter at a second location within the body lumen, and re-deploying the anchor portion of the sensor assembly from the distal end of the delivery catheter such that the anchor portion re-assumes the expanded configuration.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
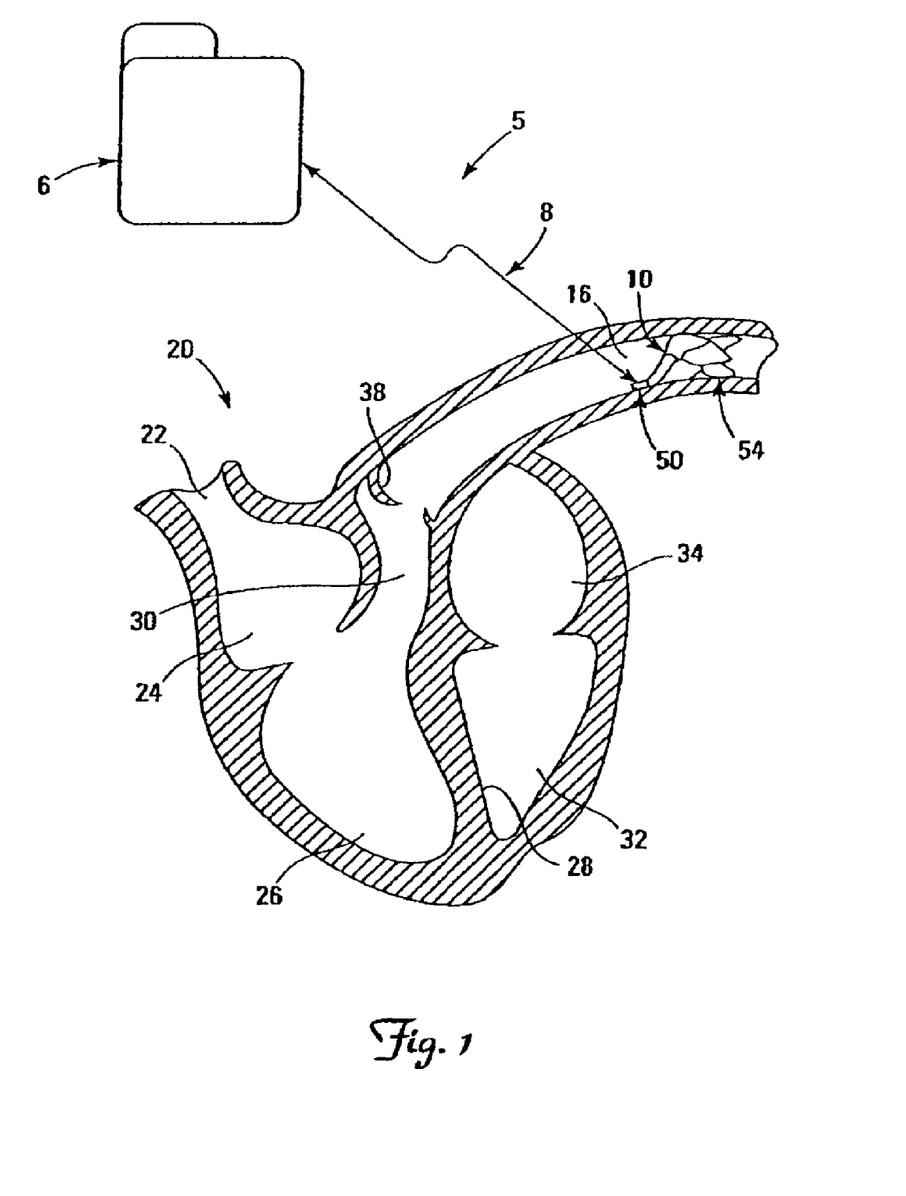
FIG. 1 is a schematic view of a cardiac rhythm management system including a pulse generator and an implantable sensor module implanted within a pulmonary artery of a heart according to one embodiment of the present invention.

FIG. 1 is a schematic view of a cardiac rhythm management system 5 including a pulse generator 6, a communication link 8, and an implantable sensor assembly 10 implanted within a pulmonary artery 16 of a heart 20 according to one embodiment of the present invention. As is known in the art, the pulse generator 6 is typically implanted subcutaneously at an implantation location in the patient's chest or abdomen. As shown, the heart 20 generally includes a superior vena cava 22, a right atrium 24, a right ventricle 26, a ventricular septum 28, a right ventricular outflow tract 30, a left ventricle 32 and a left atrium 34. As shown, the right ventricular outflow tract 30 leads to the pulmonary artery 16, which is separated from the right ventricle by a pulmonary artery valve 38.

The pulse generator 6 may be any implantable medical device known in the art or later developed, delivering an electrical therapeutic stimulus to the patient. In one embodiment, the pulse generator 6 is a pacemaker. In another embodiment, the pulse generator is an implantable cardiac defibrillator. In still other exemplary embodiments, the pulse generator 6 includes both pacing and defibrillation capabilities. In the illustrated embodiment, the pulse generator 6 and the implantable sensor assembly 10 are communicably coupled by the communication link 8, which may be a wired or wireless communication link.

As shown in FIG. 1, the sensor assembly 10 includes an implantable sensor 50 and an anchor 54 coupled to the sensor 50. As will be discussed in detail below, the anchor 54 is an expandable structure configured to assume a collapsed configuration for transvenous delivery of the sensor assembly 10 to the desired implantation location (e.g., via a delivery catheter), and an expanded configuration, illustrated in FIG. 1, in which the anchor 54 engages an inner surface of the pulmonary artery 16. The anchor 54 is further advantageously configured to facilitate retraction of the anchor 54 back within the delivery catheter after initial deployment so that the sensor assembly 10 can be repositioned within the same or a different vessel, or alternatively, removed from the patient altogether.

In the embodiment illustrated in FIG. 1, the sensor assembly 10 is implanted in the patient's main pulmonary artery 16. In other embodiments, the sensor assembly 10 may be implanted in a branch of the pulmonary artery 16 (e.g., the right or left pulmonary artery). In other embodiments, the sensor assembly 10 may be implanted in other regions of the patient's vasculature or in other body lumens.

The sensor 50 is configured to communicate with the pulse generator 6 via the communication link 8, which may be wired or wireless. Various types of wireless communication circuitry are well known in the art, and the specific type and/or style of wireless communication that can be used is not limited. For example, ultrasonic waves, acoustic communications, radio frequency communications, and the like may be used. In one embodiment, the sensor 50 includes an acoustic transmitter/receiver configured for acoustic telemetry, which transmitter/receiver is configured to transmit and/or receive ultrasonic signals to/from the pulse generator 6. In some embodiments, the sensor 50 may be configured to communicate with one or more other implantable medical devices (e.g., another pulse generator or other therapeutic device such as a drug delivery device) via other wired or wireless communication links. In still other embodiments, the sensor 50 is configured to communicate with devices external to the patient's body via wireless communication links.

The sensor 50 may be configured to perform one or more designated functions, which may include taking one or more physiological measurements. The sensor 50 may be configured to measure any known physiologic parameters such as, for example, blood pressure, temperature, blood or fluid flow, strain, electrical, chemical, or magnetic properties within the body. The specific parameters to be measured, and thus the implantation site for the sensor assembly 10, are determined based on the particular therapeutic needs of the patient. In one exemplary embodiment, the sensor 50 may be configured to measure blood pressure in the pulmonary artery 16 (e.g., as illustrated in FIG. 1). In the illustrated embodiment, the sensor 50 is adapted to store and/or transmit blood pressure data to the pulse generator 6 or a device (e.g., a monitor or programmer) located external to the patient's body.

Figure 2A:
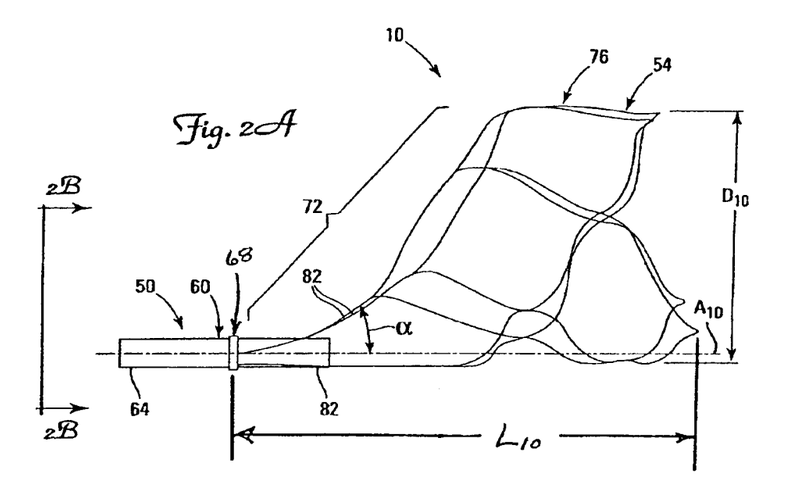
FIGS. 2A and 2B are side and proximal end views, respectively, of the sensor assembly shown implanted in FIG. 1.
Figure 2B:
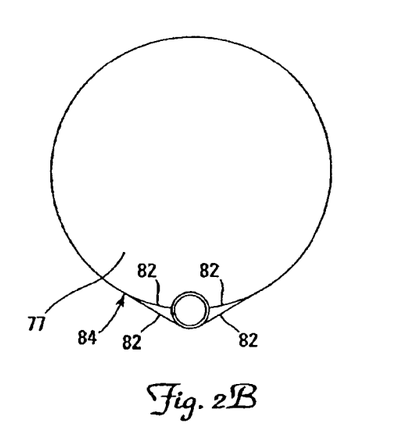

FIGS. 2A and 2B are side and proximal end views, respectively, of the sensor assembly 10 in its expanded configuration according to one embodiment of the present invention. As shown in FIGS. 2A-2B, the sensor 50 includes a housing 60 defining a proximal end 64, and the anchor 54 includes a proximal hub portion 68, an intermediate portion 72, and a distal portion 76. In the illustrated embodiment, the hub portion 68 is coupled to the sensor housing 60. In other embodiments, the sensor 50 may be coupled to other portions of the anchor 54 (e.g., near the distal end of the distal portion 76).

As shown, the intermediate portion 72 extends both distally and radially from the hub portion 68, and the distal portion 76 extends distally from the intermediate portion 72, forming a continuous transition from the intermediate portion 72 to the distal portion 76. In the illustrated embodiment, the intermediate portion 72 is formed from a plurality of elongated struts 82 extending distally and radially from the hub portion 68 In this configuration, the struts 82 are effectively hingedly connected to the hub portion 68, which permits the anchor 54 to be collapsed upon being retracted into a delivery catheter. As further shown, the distal portion 76 extends distally from the intermediate portion 72, and includes a plurality of elongate, arcuate members interconnected at approximately their mid-sections to form a generally tubular stent-like structure defining a lumen 77 for the flow of body fluids (e.g., blood) through the vessel (e.g., the pulmonary artery) in which the sensor assembly 10 is implanted. When in the expanded configuration as illustrated, at least the stent-like distal portion 76, and in some embodiments, at least portions of the struts 82 making up the intermediate portion 72, are adapted to direct a radial force against and engage the inner surface of the pulmonary artery (or other vessel) to fixate the sensor assembly 10 therein.

As shown, the proximal hub portion 68, and thus the sensor 50 attached thereto, is radially positioned at or proximate an outer periphery 84 of the anchor 54. Thus, in the illustrated embodiment, the sensor 50 will be located at or very near the wall of the vessel (e.g., the pulmonary artery) in which the sensor assembly 10 is implanted. Thus, as can perhaps be best seen in FIG. 2B, the lumen 77 formed by the anchor 54 is substantially unobstructed by other portions of the anchor assembly 10, and thus the lumen 77 provides a substantially unobstructed conduit for blood flow, passage of other medical devices (e.g., catheters, electrical leads), and the like.

In the illustrated embodiment, the proximal hub portion 68 is a generally annular structure and extends circumferentially around the housing 60 of the sensor 50. In other embodiments, the hub portion 68 may not extend completely around the sensor housing 60. In still other embodiments, the annular structure may be omitted from the hub portion 68. For example, the hub portion 68 may include generally linear members joined at or near the proximal end of the anchor 54, which members may diverge to form the intermediate portion of the anchor 54.

The anchor 54 may be coupled to the sensor 50 by any methods known in the art. For example, the anchor may be welded, brazed, soldered, adhesively bonded, or attached to the sensor housing 60 by crimping or using a mechanical fastening structure such as a snap-fit ring. Alternatively, the sensor housing 60 may be formed integrally with the anchor 54, or portions thereof. In short, the present invention does not require any particular method of coupling the sensor 50 and the anchor 54. Furthermore, in some embodiments, the sensor 50 may be frictionally coupled to the anchor (e.g., by designing an interference fit between the sensor 50 partially and the annular hub portion 68 as illustrated in FIGS. 2A-2B). Such embodiments may facilitate removing and/or replacing the sensor 50 while leaving the anchor 54 in its implanted location in a patient's vasculature.

As further shown in FIG. 2A, in the expanded configuration of the anchor 54, the struts 82 of the intermediate portion 72 radiate distally and outwardly with respect to the hub portion 68, such that at least the portion of the intermediate portion 72 nearest the hub portion 68 forms a generally oblique angle α with respect to an axis $A_{10}$ extending longitudinally through the hub portion 68. As will be explained in more detail below, the sloped orientation of the intermediate portion 72 with respect to the axis $A_{10}$ advantageously facilitates retracting the anchor 54 within a delivery sheath after deployment, such that the sensor assembly 10 can be repositioned and/or removed from the body entirely, if desired, after an initial deployment. For example, a specialized stylet or other retaining element can be releasably coupled to the proximal end 64 of the sensor 50 (or to the proximal hub portion 68 of the anchor 54), providing a means for retracting the anchor 54 back within a delivery catheter after deployment.

The specific dimensions of the anchor 54 will vary depending on the particular implantation location and the required fixation strength. In general, the anchor 54 has an expanded outer distal portion diameter $D_{10}$ and a length $L_{10}$ selected to impart a radial force on and to frictionally engage the inner surface of the target vessel in which the sensor assembly 10 is implanted. For example, as discussed above, in one embodiment, the sensor assembly 10 is configured for implantation in the pulmonary artery 16. In various exemplary embodiments, the anchor 54 has a length $L_{10}$ of from about 20 millimeters to about 60 millimeters and an expanded diameter $D_{10}$ of from about 16 millimeters to about 50 millimeters. In one embodiment, the length $L_{10}$ is about 50 millimeters and the expanded diameter $D_{10}$ is about 38 millimeters. In one embodiment, the length $L_{10}$ is about 50 millimeters and the expanded diameter $D_{10}$ is about 32 millimeters. It is emphasized, however, that these examples are illustrative only, and that particular implantation locations may call for other anchor lengths $L_{10}$ and expanded diameters $D_{10}$.

Figure 3A:
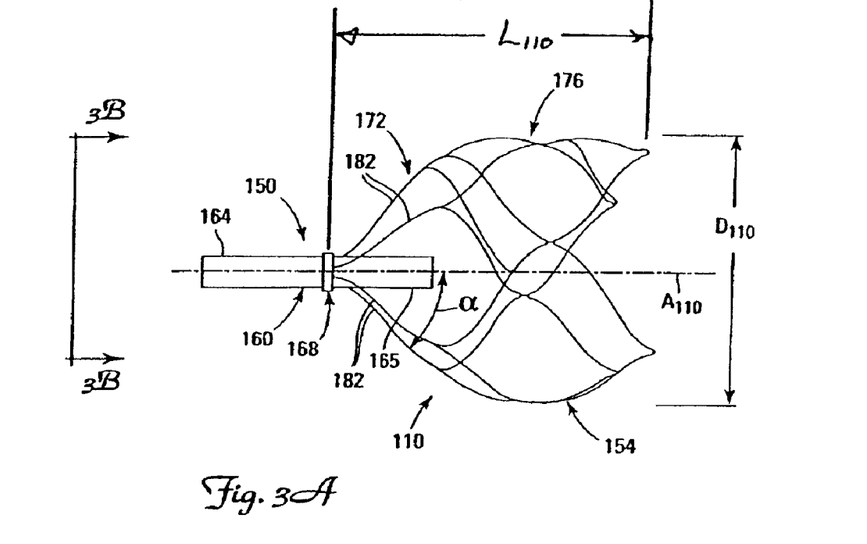
FIGS. 3A and 3B are side and proximal end views, respectively, of a sensor assembly according to another embodiment of the present invention.
Figure 3B:
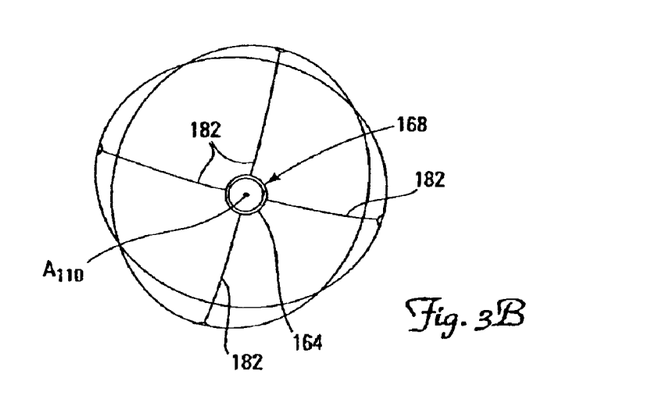

FIGS. 3A and 3B are side and proximal end views, respectively, of a sensor assembly 110 according to another embodiment of the present invention. As shown in FIGS. 3A-3B, the sensor assembly 110 includes a sensor 150 and an anchor 154, which like the anchor 54 described above, includes a housing 160 and a proximal end 164, and the anchor 154 includes a proximal hub portion 168, an intermediate portion 172, and a distal portion 176. In the illustrated embodiment, the hub portion 168 is coupled to the sensor housing 160. In other embodiments, the sensor 150 may be coupled to other portions of the anchor 154. The distal portion 176 includes a plurality of interconnected, undulating members arranged to form a generally tubular stent-like structure providing a lumen 177 for the flow of body fluids (e.g., blood) through the vessel (e.g., the pulmonary artery) in which the sensor assembly 110 is implanted.

The sensor assembly 110 is in many respects similar to the sensor assembly 10 described above, with the primary exception being that in the sensor assembly 110, the hub portion 168 is radially located within the lumen 177 formed by the distal portion 176, and the intermediate portion 172 includes a plurality of struts 182 extending distally and radially from the hub portion 168 in a manner similar to spokes on a wheel. In the illustrated embodiment, the hub portion 168 is substantially centrally located in the lumen 177. In other embodiments, the hub portion 168 may be offset from the radial center of the lumen 177.

Similar to the anchor 54, in the expanded configuration shown in FIGS. 3A and 3B, the struts 182 of the anchor intermediate portion 172 of the anchor 154 radiates distally and outwardly, such that the intermediate portion 172 generally forms an oblique angle α with respect to an axis $A_{110}$ extending longitudinally through the hub portion 168. Thus, as with the anchor 54, the sloped orientation of the intermediate portion 172 with respect to the axis $A_{110}$ advantageously facilitates retracting the anchor 154 within a delivery sheath after deployment.

As with the anchor 54 described above, the anchor 154 has an expanded outer distal portion diameter $D_{110}$ and a length $L_{110}$ selected to impart a radial force on and to frictionally engage the inner surface of the target vessel in which the sensor assembly 10 is implanted. In one embodiment, the sensor assembly 110 is configured for implantation in the pulmonary artery 16, and the anchor 154 has a length $L_{110}$ of from about 20 millimeters to about 60 millimeters and an expanded diameter $D_{110}$ of from about 16 millimeters to about 50 millimeters. In one embodiment, the length $L_{110}$ is about 50 millimeters and the expanded diameter $D_{110}$ is about 38 millimeters. In one embodiment, the length $L_{110}$ is about 50 millimeters and the expanded diameter $D_{110}$ is about 32 millimeters. It is emphasized, however, that these examples are illustrative only, and that particular implantation locations may call for other anchor lengths $L_{110}$ and expanded diameters $D_{110}$.

Figure 4:
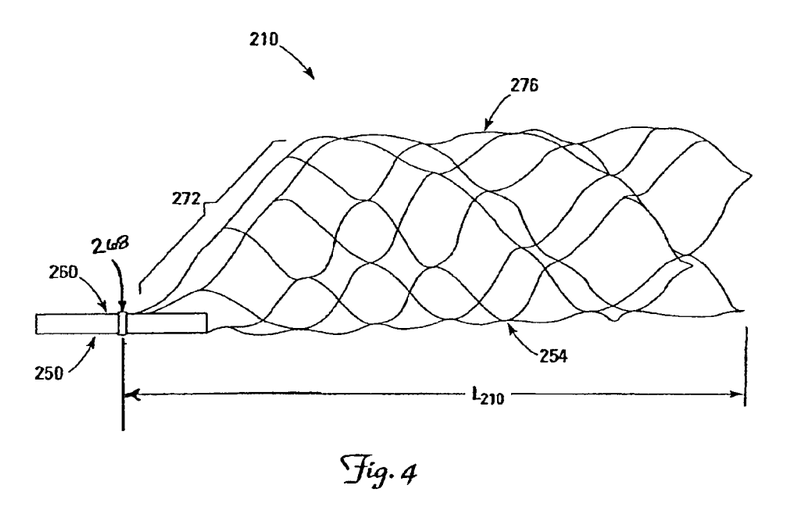
FIG. 4 is a side view of a sensor assembly according to another embodiment of the present invention.

FIG. 4 is a side view of a sensor assembly 210 according to another embodiment of the present invention. As shown in FIG. 4, the sensor assembly 210 includes a sensor 250 and an anchor 254. The sensor 250 includes a housing 260 and a proximal end 164, and the anchor 254 includes a proximal hub portion 268, an intermediate portion 272, and a distal portion 276. In the illustrated embodiment, the hub portion 268 is coupled to the sensor housing 260, although in other embodiments, the sensor 250 may be coupled to the anchor 254 at other locations.

As can be seen in FIG. 4, the sensor assembly 210 is configured in a manner substantially similar to the sensor assembly 10 described above, with the primary difference being the elongated distal portion 276 of the anchor 254 as compared to the anchor 54. The elongated distal portion 276 provides an increased fixation strength due to the increased surface area for engaging the vessel inner surface, as compared to the distal portion 76 of the anchor 54. In one embodiment of the sensor assembly 210 configured for implantation in the patient's pulmonary artery, the anchor 254 has a length $L_{210}$ of from about 70 to about 90 millimeters. In one embodiment, the length $L_{210}$ is about 80 millimeters.

Thus, when in their expanded configurations as illustrated in the respective figures, the intermediate portions and the stent-like distal portions of the anchors 54, 154, and 254 form radially expandable means for engaging the inner surface of the vessel (e.g., the pulmonary artery) to fixate the respective sensor assembly 10 therein.

The respective sensors and anchors of the sensor assemblies 10, 110, 210 described above can be made of any biocompatible materials suitable for similar implantable medical devices, whether now known or later developed. For example, in various embodiments, any or all of the sensor housings 60, 160, and/or 260 may be made of any biocompatible materials suitable for use for hermetic housings for other implantable medical devices. Such materials include, without limitation, titanium, stainless steel, biocompatible polymers, and the like. It will be appreciated that the particular design requirements of the implantable medical device and the associated anchor will primarily dictate the material selected.

The stent-like anchors 54, 154, and/or 254 described above can be self-expanding or balloon expandable, and can be made from any materials, whether now known or later developed, suitable for use in cardiovascular stents or similar implantable devices. By way of example only, suitable materials include stainless steel and a wide variety of alloys and polymers. For self-expanding embodiments, the anchors 54, 154, 254 are made at least partially from materials having desirable shape memory and/or superelastic properties. Exemplary materials exhibiting suitable shape memory and superelasticity include shape memory polymers and nickel-titanium shape memory alloys such as nitinol. In some embodiments, the anchors 54, 154, and/or 254 are laser cut from a nitinol tube. In other embodiments, the anchors 54, 154, and/or 254 may be formed substantially from wire stock. Other suitable materials will be ascertained by those skilled in the art based on the foregoing.

For all of various embodiments of the present invention, the size of the anchor structure, in both the collapsed and expanded configurations, will generally be determined based on the particular patient anatomy. In some embodiments, the anchors 54, 154, and/or 254 are designed and sized to frictionally engage the inner surface of the vessel wall upon expansion. In one embodiment, e.g., where the anchoring structures are designed to be secured in the pulmonary artery 16, which branches and tapers as it flows toward the lungs, the anchoring structure can be placed in the pulmonary artery, and then allowed to flow with blood stream until the anchoring structure lodges in a desired location. Once secured, the sensor can collect the desired data measurements. Of course, as one skilled in the art will appreciate, the anchoring structure can be placed in other blood vessels, or other bodily lumens.

Figure 5A:
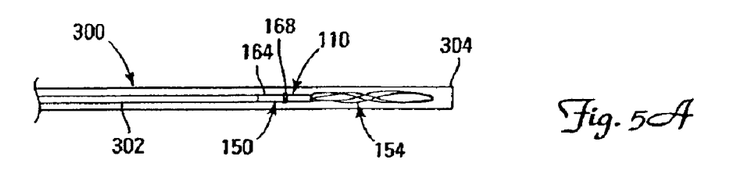
FIGS. 5A-5D are side views of the sensor assembly of FIGS. 3A-3B being deployed from a delivery catheter according to one embodiment of the present invention.

FIGS. 5A-5D are side views illustrating, schematically, the sensor assembly 110 being deployed from a delivery catheter 300. As shown in FIG. 5A, the sensor assembly 110 is initially retained within the delivery catheter 300 with the anchor 154 in a collapsed configuration and a tether 302 releasably coupled to the proximal end 164 of the sensor 150. The tether 302 can be a stylet, guidewire, or similar structure having a distal mechanism adapted to releasably engage the sensor 150 (or the hub portion 168) as the sensor assembly 110 is deployed through the catheter 300. For example, the tether 302 may include any of the structures disclosed in the co-pending and commonly assigned U.S. Provisional Patent Applications 60/844,953 titled "DELIVERY SYSTEM FOR AN IMPLANTABLE PHYSIOLOGIC SENSOR" filed Sep. 15, 2006, and 60/844,948 titled "MECHANISM FOR RELEASABLY ENGAGING AN IMPLANTABLE MEDICAL DEVICE FOR IMPLANTATION" filed Sep. 15, 2006, the contents of which are incorporated herein by reference for all purposes.

The tether 302 allows the user (e.g., a physician or other medical professional) to control the position of the sensor assembly 110 with respect to the catheter 300. For example, the tether 302 can be pushed distally relative to the catheter 300 to advance the anchor 154 beyond a distal end 304 of the catheter 300. Alternatively, the catheter 300 can be retracted in a proximal direction while the tether 302 is held in place. In either approach, in the illustrated embodiment, the anchor 154 self-expands to its expanded configuration upon being extended beyond the distal end 304 of the catheter 300.

Figure 5B:
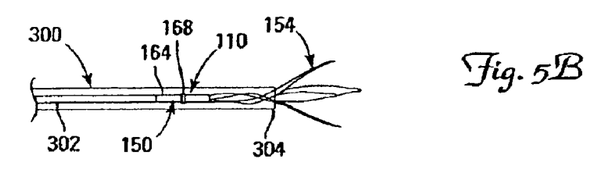
Figure 5C:
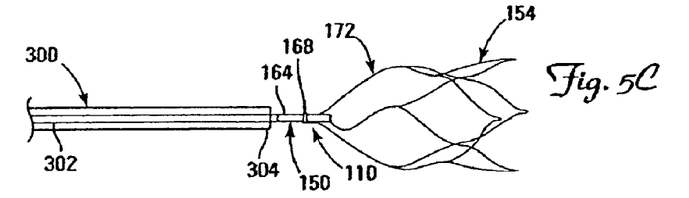

FIG. 5B illustrates the sensor assembly 110 with the anchor 154 partially deployed from the distal end 304 of the catheter 300. In the embodiment of FIG. 5B, the anchor 154 is self-expanding, and in that respect is similar to cardiovascular stents as are known in the art. FIG. 5C illustrates the sensor assembly 110 fully deployed from the distal end 304 of the catheter 300, with the tether 302 still coupled to the proximal end 164 of the sensor 150. As shown in FIG. 5C, the anchor 154 is fully expanded to its expanded configuration such that it can engage an inner surface of a vessel (e.g., the pulmonary artery) to secure the sensor assembly 110 therein. FIG. 5C further illustrates the sloped configuration of the intermediate portion 172 with respect to the sensor 150 and the longitudinal axis $A_{110}$ extending through the proximal portion 168 (see FIG. 3A), and in turn, the delivery catheter 300.

Figure 5D:
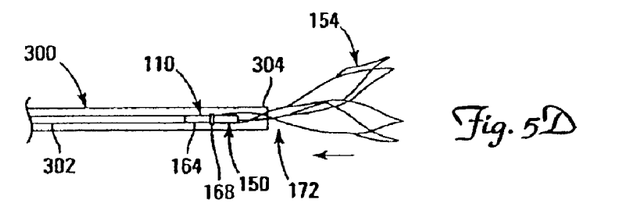

FIG. 5D illustrates the sensor assembly 110 partially retracted within the catheter 300. As shown in FIG. 5D, the anchor 154 can re-assume its collapsed configuration and be retracted back into the catheter 300 after being fully deployed as shown in FIG. 5C. This retractability is enabled by the configuration of the intermediate portion 172 of the anchor 154, and more particularly, the oblique angle of the intermediate portion 172 with respect to the longitudinal axis $A_{110}$ extending through the proximal hub portion 168 (see FIG. 3A). The illustrated configuration of the hub portion 168 and the intermediate portion 172 in effect hingedly connects the members making up the intermediate portion 172 to the hub portion 168, allowing the anchor 154 to be collapsed as it is withdrawn back into the catheter 300. It will be appreciated that the anchor 154 can subsequently be re-deployed at this or a different location within the vasculature, if desired.

FIGS. 6A through 6D are perspective, side, top, and distal end views, respectively, of an anchor 354 according to another embodiment of the present invention. As shown in FIGS. 6A-6D, the anchor 354 includes a proximal hub portion 368, an intermediate portion 372, and a distal portion 376. As with the anchors described above, the intermediate portion 372 extends distally from the hub portion 368, and the distal portion 376 extends distally from the intermediate portion 372. In the illustrated embodiment, the hub portion 368 includes an annular ring 379 adapted to be coupled to an implantable medical device (e.g., an implantable physiologic sensor such as the sensors 50, 150, 250 described above). As shown, the hub portion 368 further includes a plurality (in this case, two) shank members 380, 382 extending distally from the annular ring 379. As with the anchor embodiments described above, the annular ring 379 may, in some embodiments, be omitted. Alternatively, the hub portion 368 may include an alternative structure adapted for coupling the anchor 354 to the respective implantable medical device.

As shown, the intermediate portion 372 includes a pair of hinge elements 384, 386 extending distally from the shank members 380, 382, respectively. As further shown, the hinge element 384 includes a pair of diverging arms 388, 389 hingedly connected at the distal end of the shank member 380, and the hinge element 386 includes a pair of diverging arms 390, 391 hingedly connected at the distal end of the shank member 382.

Figure 6A:
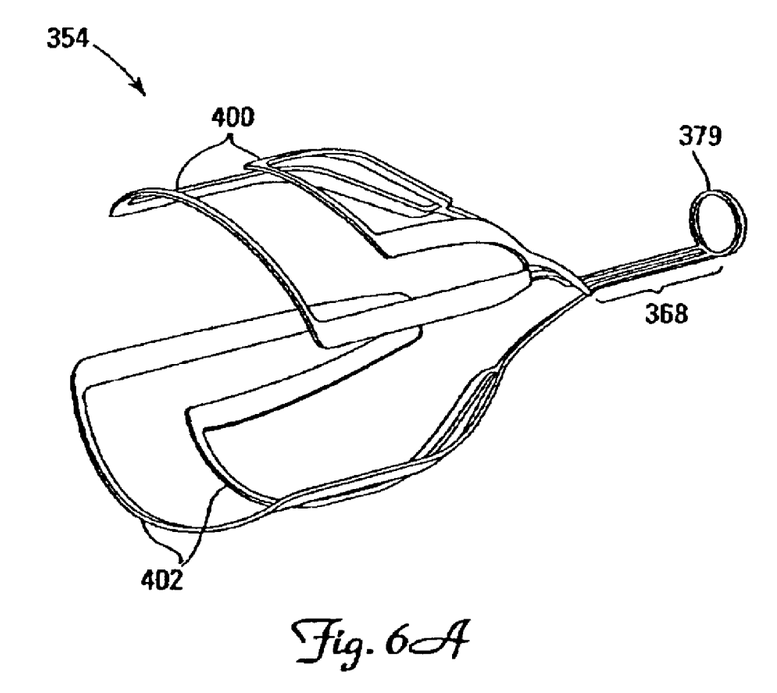
FIGS. 6A-6D are perspective, side, top, and distal end views, respectively, of an anchor for a sensor assembly or other implantable medical device according to another embodiment of the present invention.
Figure 6B:
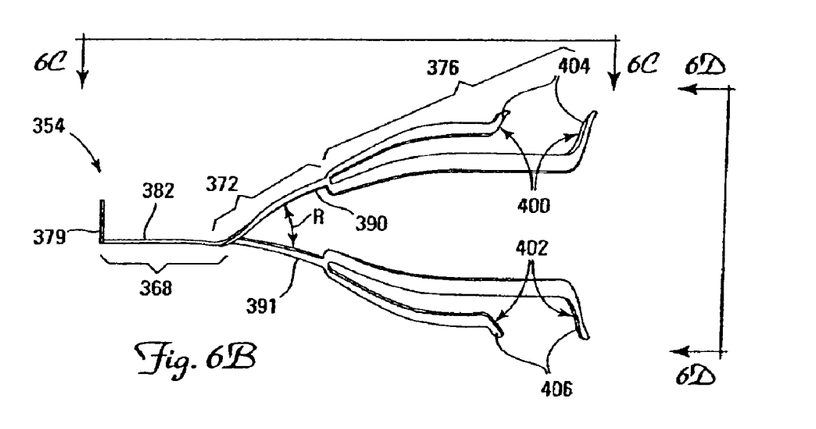
Figure 6C:
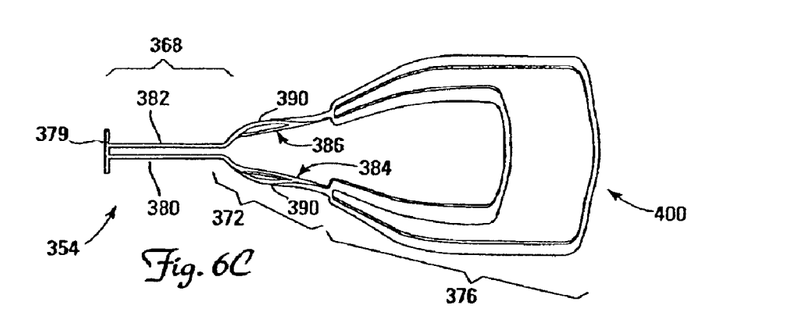
Figure 6D:
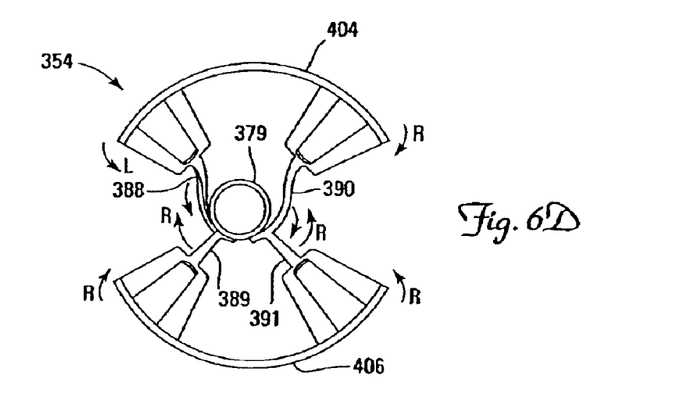

The distal portion 376 includes a pair of vessel engaging structures 400, 402 which as illustrated are in the form of nested jaw structures extending from the distal ends of the diverging arms 388, 390 and 389, 391, respectively. The jaw structures further include peripheral surfaces 404, 406 adapted to frictionally engage the inner surfaces of the target vessel when the anchor is in its expanded configuration as shown in FIGS. 6A-6C. Thus, when in its expanded configuration as illustrated, in the respective figures, the intermediate portion 372 and the distal portion 376 form radially expandable means for engaging the inner surface of the vessel (e.g., the pulmonary artery) to fixate the sensor assembly therein.

The hinged configuration of the anchor 354 and the design of the distal portion 376 allows the intermediate and distal portions 372, 376 to be collapsed inwardly, as indicated by the arrows R in FIGS. 6A and 6C, for delivery of the anchor 354 through a catheter or similar device. Additionally, the anchor 354 is adapted to self-expand to the expanded configuration illustrated in FIGS. 6A-6C for securing an implantable medical device (not shown) attached to the hub portion 368 within a target vessel. Still additionally, similarly to the anchors 54, 154, and 254 (see FIGS. 5A-5D) described above, the hinged configuration of the intermediate portion 372 and the oblique orientation of the intermediate portion 372 relative to the proximal portion 368 allows the anchor 354 to be collapsed when retracted back within a delivery catheter after initial deployment.

The anchor 354 may be made from any of the materials described above in connection with the anchors 54, 154, and 254. Additionally, as will be appreciated, the anchor 354 may be formed by any methods known in the art or later developed for manufacturing expandable implantable medical device anchors and the like.

Figure 7:
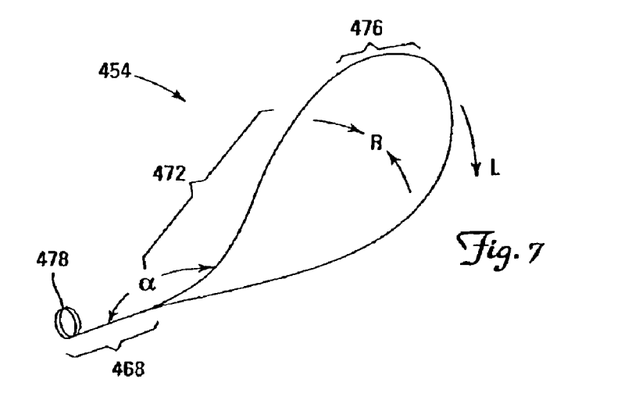
FIGS. 7-10 are schematic perspective views of alternative anchors for a sensor assembly or other implantable medical device according to other embodiments of the present invention.

FIG. 7 is a schematic perspective view of a re-positionable anchor 454 in an expanded configuration according to another embodiment of the present invention. As shown in FIG. 7, the anchor 454 generally takes the form of a teardrop-shaped loop when in the expanded configuration, and includes a proximal hub portion 468, an intermediate portion 472, and a distal portion 476. As with the anchors described above, the intermediate portion 472 extends distally from the hub portion 468, and the distal portion 476 extends distally from the intermediate portion 472 In the illustrated embodiment, the hub portion 468 includes an annular ring 478 forming an attachment structure (such as the annular rings shown in FIGS. 2A and 6A-6C) adapted for coupling to the anchor 454 to an implantable medical device (e.g., an implantable physiologic sensor such as the sensors 50, 150, 250 described above).

As is apparent from FIG. 7, the anchor 454 transitions gradually from the hub portion 468 to the intermediate portion 472, which forms an oblique angle α with respect to the hub portion 468, which itself is desirably oriented generally parallel to the target vessel (e.g., the pulmonary artery 16, see FIG. 1) in which the anchor 454 is implanted. This configuration, and the loop shape of the anchor 454 in general, permit the anchor 454 to be collapsed radially and longitudinally (as indicated by the arrows R and L in FIG. 7) when retracted back within a delivery catheter or sheath after initial deployment. Thus, as with the anchors 54, 154, 254, and 354 described above, the anchor 454 allows an implantable medical device (e.g., an implantable sensor) to be repositioned within a patient's vasculature after initial deployment from the delivery catheter.

Figure 8:
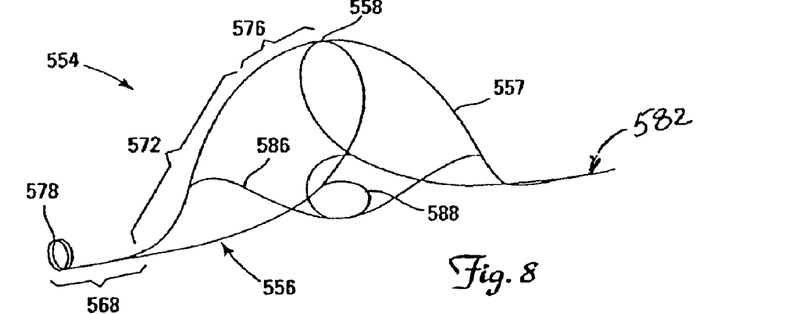

FIG. 8 is a schematic perspective view of a repositionable anchor 554 in an expanded configuration according to another embodiment of the present invention. As shown in FIG. 8, the anchor 554 includes a pair of loops 556, 557 arranged back-to-back and connected at a connection location 558 at or near the vertices of the anchor 454 and the loop loops 556, 557. As can be seen in FIG. 8, at least the loop 556 is substantially similar in form and construction as the anchor 454 described above, and includes a proximal hub portion 564, an intermediate portion 572, and a distal portion 576, which portions are configured substantially similar or identical to the corresponding portions of the anchor 454 described above. In the illustrated embodiment, the hub portion 568 includes an annular ring 578 for coupling to the anchor 554 to an implantable medical device as described above. As can be further seen, the loop 557 is, in the illustrated embodiment, essentially a mirror image of the loop 556 and includes a distal end portion 582. The anchor 554 further includes coil-shaped connecting members 586, 588 extending between and connecting the loops 556, 557.

The loops 556, 557 of the anchor 554 are configured to operate in substantially the same manner as the anchor 454 above. In particular, the loops 556, 557 permit the anchor 554 to be collapsed radially and longitudinally when retracted back within a delivery catheter or sheath after initial deployment. Additionally, in some embodiments, the distal end portion 582 may provide a structure for the attachment of an implantable sensor or other implantable medical device. Thus, the embodiment of FIG. 9 advantageously permits the attachment of multiple implantable sensors, if desired. Alternatively, an implantable sensor may be attached to the distal end portion 582 and not to the proximal hub portion 568, which may be used for other purposes (e.g., for coupling the anchor 554 to a tether or retaining element for deployment of the anchor and implantable medical device attached thereto).

Figure 9:
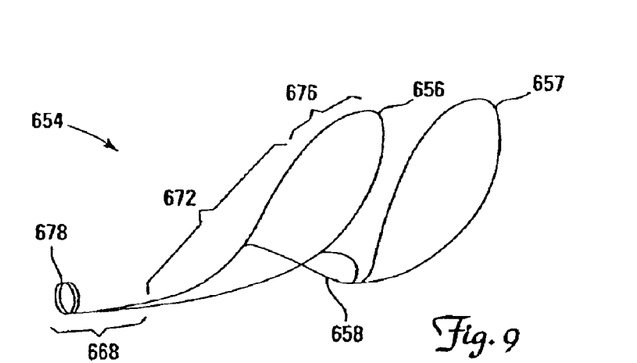

FIG. 9 is a schematic perspective view of a repositionable anchor 654 in an expanded configuration according to another embodiment of the present invention. As can be seen in FIG. 9, the anchor 654 is another variation of the anchor 454, and includes a pair of loops 656, 657 longitudinally spaced and connected by an elongate connecting element 658. As shown, at least the loop 656 is substantially similar in form and construction as the anchor 454 described above, and includes a proximal hub portion 664, an intermediate portion 672, and a distal portion 676, which portions are configured substantially similar or identical to the corresponding portions of the anchor 454 described above. As further shown, the proximal hub portion 668 includes an annular ring 678 for coupling to the anchor 654 to an implantable medical device as described above.

Figure 10:
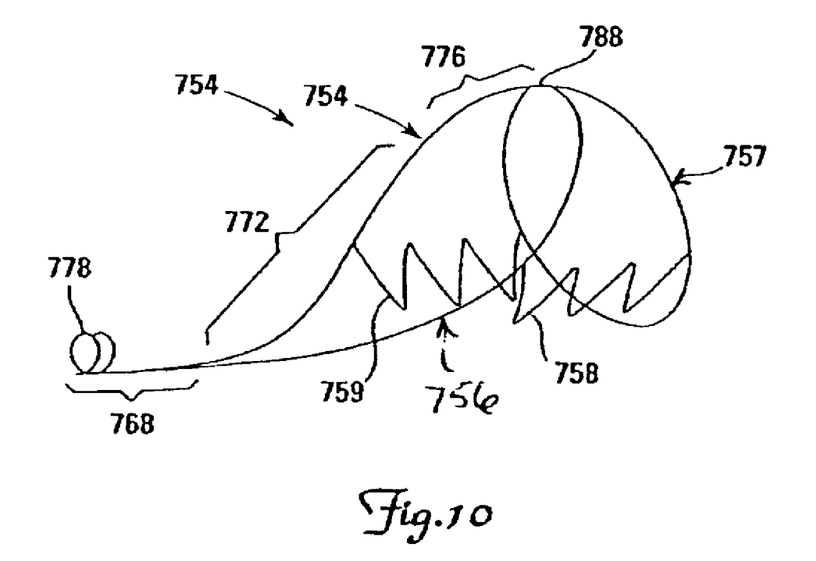

FIG. 10 is a schematic perspective view of a repositionable anchor 754 in an expanded configuration according to another embodiment of the present invention. As can be seen in FIG. 10, the anchor 754 is another variation of the anchor 454, and includes a pair of loops 756, 757 longitudinally spaced and connected by elongate connecting elements 758, 759 disposed along the periphery of the anchor with the loops 756, 757 in their expanded configurations. At least the loop 756 is substantially similar in form and construction as the anchor 454 described above, and includes a proximal hub portion 768, an intermediate portion 772, and a distal portion 776, which portions are configured substantially similar or identical to the corresponding portions of the anchor 454 described above. In the illustrated embodiment, the hub portion 768 includes an annular ring 778 for coupling to the anchor 754 to an implantable medical device as described above. As further shown, the distal portion 776 of the loop 756 is directly attached to the loop 757 at an attachment location 788.

Any of the loop-shaped anchors 454, 554, 654, and 754 are configured to operate in substantially the same or an identical manner as the anchors 54, 154, 254, and 354 described above. In particular, all of the foregoing anchors are configured such that they can be collapsed radially and longitudinally (such as indicated by the arrows R and L in FIG. 7) when retracted back within a delivery catheter or sheath after initial deployment. Thus, as with the anchors 54, 154, 254, and 354 described above, these anchors allow an implantable medical device (e.g., an implantable sensor) to be repositioned within a patient's vasculature after initial deployment from the delivery catheter. Thus, when in their expanded configurations as illustrated in the respective figures, the intermediate portions and the distal portions of the anchors 454, 554, 654, and 754 form radially expandable means for engaging the inner surface of the vessel (e.g., the pulmonary artery) to fixate the respective sensor assembly therein.

The anchoring structures described above allow the sensor, or other implantable medical device, to be anchored and secured in any part of the vascular system. In one particular embodiment, assembly can be delivered to the target implantation site within the vascular system using known catheterization techniques.

Figure 11:
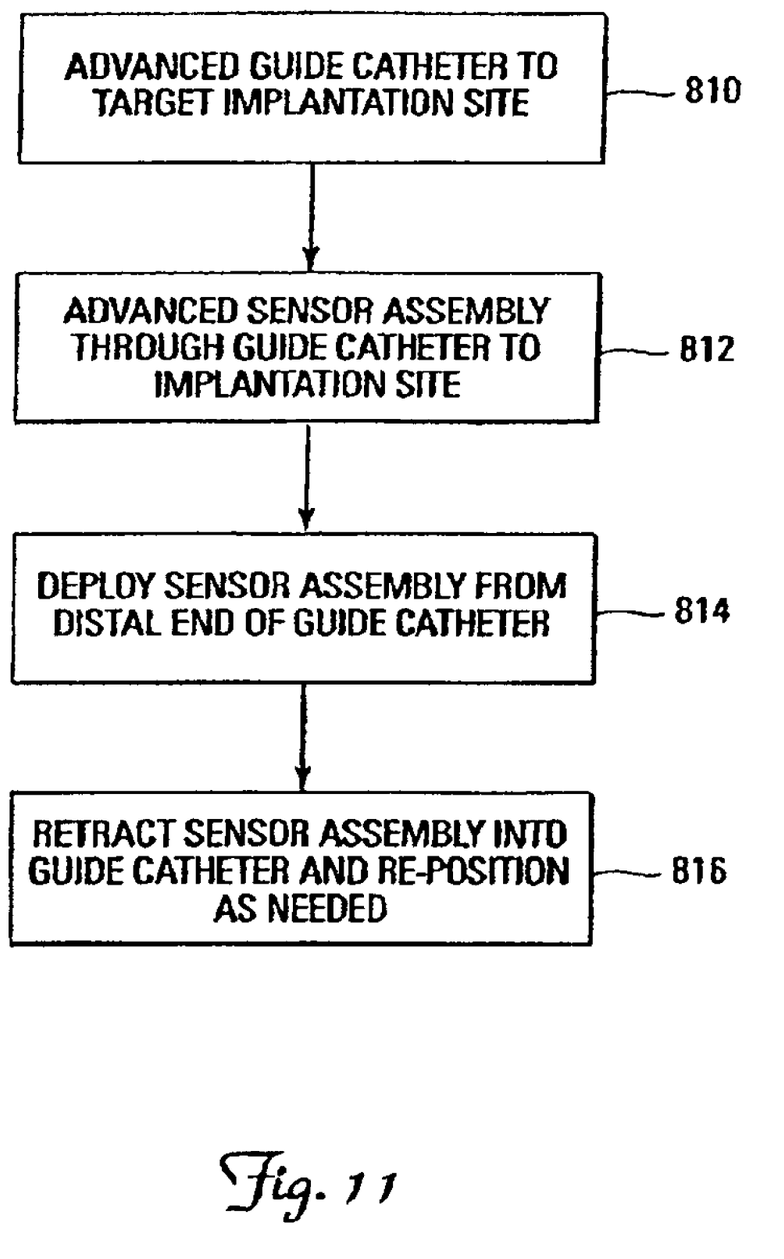
FIG. 11 is a flow chart illustrating a method of deploying an implantable sensor assembly according to one embodiment of the present invention.

FIG. 11 is a flow chart illustrating a method of deploying an implantable sensor assembly (e.g., the assembly 10, 110, 210, or an assembly utilizing one of the anchors 354, 454, 554, 654, 754) according to one embodiment of the present invention. In one exemplary embodiment, the sensor assembly is implanted in the pulmonary artery 16 (see FIG. 1) or a branch thereof. As shown in FIG. 11, a guide catheter is transvenously advanced, using methods known in the art, until its distal end is positioned proximate an implantation site within the pulmonary artery 16. (Block 810) For example, in one embodiment, a Swan Ganz catheter, which includes a balloon at or near its distal end, may be inserted into the venous system and floated with the blood flow into and through the heart 20 out to the pulmonary artery 16. The balloon catheter can then be used to locate a guide wire and subsequently, a second guide catheter partially within the pulmonary artery 16. It is emphasized, however, that any catheterization techniques, whether now known or later developed, can be used to position the sensor assembly within the pulmonary artery 16 (or other region of the vasculature system, as appropriate).

If desired by the clinician, the sensor assembly, with a tether or other retaining structure releasably attached, can be pre-loaded into the guide catheter lumen prior to catheterization. Alternatively, the guide catheter can be positioned as desired in the patient's vasculature system, and the sensor assembly and tether can be advanced through the catheter lumen to a location proximate the distal opening of the catheter. (Block 812)

The sensor assembly, or at least the anchor, can then be deployed, with the tether still attached, from the distal end of the guide catheter. (Block 814) For example, the sensor assembly can be deployed by retracting the guide catheter while holding the tether, and thus the sensor assembly, in position, or by pushing the tether and sensor assembly distally out the distal end of the catheter. Once released from the guide catheter, the anchor may self-expand to assume its expanded configuration and engage the inner surface of the pulmonary artery 16. Alternatively, where a balloon-expandable anchor is used, the anchor can be expanded by inflating a balloon, as is known in the art for, example, expanding balloon-expandable vascular stents.

If desired, the tether can then be released from the sensor assembly, and the tether and guide catheter can be retracted from the patient. Alternatively, if the physician determines that the sensor assembly should be removed or repositioned, the physician can retract the sensor assembly, including the anchor, back within the guide catheter by pulling the tether distally with respect to the guide catheter. (Block 816) As illustrated in FIG. 5D, the anchor will collapse as it is retracted back within the guide catheter so as to re-assume its collapsed configuration within the guide catheter. The catheter can then be re-positioned in the pulmonary artery or relocated to another area of the patient's vasculature. The anchor and/or the sensor assembly in its entirety can then be re-deployed from the guide catheter. Alternatively, the sensor assembly can be removed from the body entirely (e.g., if the sensor is determined to be not functioning as desired, or if the anchor is incorrectly sized or configured for the particular patient anatomy).

Of course, it will be appreciated that the anchor structures described above may be utilized to secure physiologic sensors and/or other implantable medical devices in any area of a patient's cardiovascular system, or in some embodiments, in other bodily lumens. That is, the anchors described above may effectively secure sensors and other devices in vessels other than the pulmonary artery and its branches.

Additionally, in some embodiments, the anchors described above may be utilized to secure therapy delivery devices (e.g., drug delivery devices, stimulation electrodes) in addition to, or in lieu of, implantable physiologic sensors. In such embodiments, the therapeutic functions are not limited to any particular type and can include, for example, ultrasound or drug delivery therapy, or any other therapy capable of being administered with an implantable medical device currently known or later developed. In some embodiments, anchoring structures may be used to place a plurality of sensors, actuators, or a combination of sensors and actuators. Placement of multiple sensors and/or actuating devices throughout the body can allow for a more comprehensive therapeutic and diagnostic system, but multiple sensors and/or actuating devices are not required.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable sensor assembly configured for delivery through a delivery catheter, the sensor assembly comprising:
    an implantable sensor;
    an anchor coupled to the sensor and adapted to assume a collapsed configuration within the delivery catheter and an expanded configuration external to the delivery catheter, the anchor including:
        a proximal hub portion;
        an intermediate anchor portion hingedly coupled to and extending distally and radially from the hub portion, the intermediate portion configured to assume a generally oblique angle with respect to the hub portion when the anchor is in the expanded configuration; and a distal anchor portion extending distally from the intermediate portion and adapted to engage an inner surface of a vessel when the anchor is in the expanded configuration;

wherein the intermediate portion is configured to allow the anchor to be retracted within the delivery catheter and to assume the collapsed configuration after assuming the expanded configuration; and wherein, in the expanded configuration, the implantable sensor and proximal hub portion are radially offset from a radial center of the anchor such that the sensor is positioned at or proximate a periphery of the distal anchor portion.

2. The assembly of claim 1 wherein the anchor is coupled to the sensor at the hub portion.

3. The assembly of claim 2 wherein the sensor includes a housing, and wherein the hub portion is generally annular and is adapted to extend circumferentially around at least a portion of the sensor housing.

4. The assembly of claim 1 wherein at least the distal portion is adapted to engage an inner surface of a pulmonary artery of a patient.

5. The assembly of claim 1 wherein the sensor includes a pressure sensor.

6. The assembly of claim 5 wherein the pressure sensor is adapted to measure a pulmonary arterial blood pressure.

7. The assembly of claim 1 wherein the anchor is balloon-expandable.

8. The assembly of claim 1 wherein the anchor is self-expanding.

9. The assembly of claim 1 wherein the anchor is made from a shape memory material.

10. The assembly of claim 9 wherein the anchor is made from a shape memory nickel-titanium alloy.

11. An implantable sensor assembly comprising:
a sensor including a housing hermetically enclosing a sensor element; and
an anchor including:
    a proximal sensor attachment portion coupled to the housing; and
    radially expandable means extending from the sensor attachment portion for engaging an inner surface of a vessel;
    wherein the radially expandable means is configured to assume a collapsed configuration for delivery within a catheter and an expanded configuration external to the catheter;
    wherein the radially expandable means includes a plurality of first elongate members extending distally and radially from the sensor attachment portion at an oblique angle with respect to the sensor attachment portion when in the expanded configuration, and a plurality of second elongate members extending distally from at least one of the first elongate members, the second elongate members adapted to engage the inner surface of the vessel when in the expanded configuration; and
    wherein, in the expanded configuration, the sensor and proximal sensor attachment portion are radially offset from a radial center of the anchor such that the sensor is positioned at or proximate a periphery of the radially expandable means.

12. The assembly of claim 11 wherein the second elongate members each include at least one arcuate segment, wherein adjacent second elongate members are attached to each other at approximately a middle portion of each arcuate segment.

13. The assembly of claim 12 wherein the sensor attachment portion is generally annular and is adapted to extend circumferentially around at least a portion of the sensor housing.

* * * * *